(12) United States Patent
Brady

(10) Patent No.: US 6,723,040 B2
(45) Date of Patent: Apr. 20, 2004

(54) BOWEL PROBE & METHOD FOR CONTROLLING BOWEL INCONTINENCE

(75) Inventor: John Daniel Brady, Higgins, TX (US)

(73) Assignee: International Development Consultants, Wichita, KS (US)

( * ) Notice: Subject to any disclaimer, the term of this patent is extended or adjusted under 35 U.S.C. 154(b) by 0 days.

(21) Appl. No.: 10/222,258

(22) Filed: Aug. 16, 2002

(65) Prior Publication Data

US 2003/0176761 A1 Sep. 18, 2003

Related U.S. Application Data

(60) Provisional application No. 60/313,540, filed on Aug. 20, 2001.

(51) Int. Cl.$^7$ .................................................. A61F 2/00
(52) U.S. Cl. .................................................... 600/29
(58) Field of Search ................................ 600/473, 373, 600/593, 546, 595, 586, 391, 547, 560, 526, 522, 506, 300; 607/40, 125, 138; 442/58; 428/304.4, 421, 422, 514, 80; 55/527; 128/920; 702/188; 705/2; 106/197, 198; 264/250

(56) References Cited

U.S. PATENT DOCUMENTS

| | | | | |
|---|---|---|---|---|
| 4,380,237 A | * | 4/1983 | Newbower | 600/506 |
| 4,729,385 A | * | 3/1988 | Juncosa et al. | 600/547 |
| 4,813,422 A | * | 3/1989 | Fisher et al. | 600/473 |
| 4,951,682 A | * | 8/1990 | Petre | 600/526 |
| 5,242,747 A | * | 9/1993 | Wu | 442/58 |
| 5,277,197 A | * | 1/1994 | Church et al. | 600/546 |
| 5,335,668 A | * | 8/1994 | Nardella | 600/547 |
| 5,385,577 A | * | 1/1995 | Maurer et al. | 607/41 |
| 5,452,719 A | * | 9/1995 | Eisman et al. | 600/373 |
| 5,533,515 A | * | 7/1996 | Coller et al. | 600/593 |
| 5,617,876 A | * | 4/1997 | van Duyl | 600/595 |
| 5,833,625 A | * | 11/1998 | Essen-Moller | 600/547 |
| 5,924,984 A | * | 7/1999 | Rao | 600/373 |
| 6,096,057 A | * | 8/2000 | Klingenstein | 606/197 |
| 6,185,465 B1 | * | 2/2001 | Mo et al. | 607/138 |
| 6,228,040 B1 | * | 5/2001 | Craine | 600/586 |
| 6,321,116 B1 | * | 11/2001 | Mo et al. | 607/41 |
| 6,524,239 B1 | * | 2/2003 | Reed et al. | 600/300 |
| 2002/0072779 A1 | * | 6/2002 | Loeb | 607/40 |

* cited by examiner

Primary Examiner—Eric F. Winakur
Assistant Examiner—Nikita R Veniaminov
(74) Attorney, Agent, or Firm—Gregory J. Nelson

(57) ABSTRACT

A bowel control probe and method of detecting and preventing bowel incontinence. The probe has a body with a distal end which is permeable to gas. Conductivity sensors on the probe will establish an electrical circuit in the presence of fecal matter to send an alert signal to a control unit. The sensors may be partially shielded by a removable sleeve to reduce false alarms resulting from moisture. The control unit may issue an audible or visual alarm and may transmit a signal to a remote nursing station. An air cuff about the probe body is cyclically inflated and deflated to block passage of fecal matter and to protect tissue and capillaries in the rectal area.

23 Claims, 3 Drawing Sheets

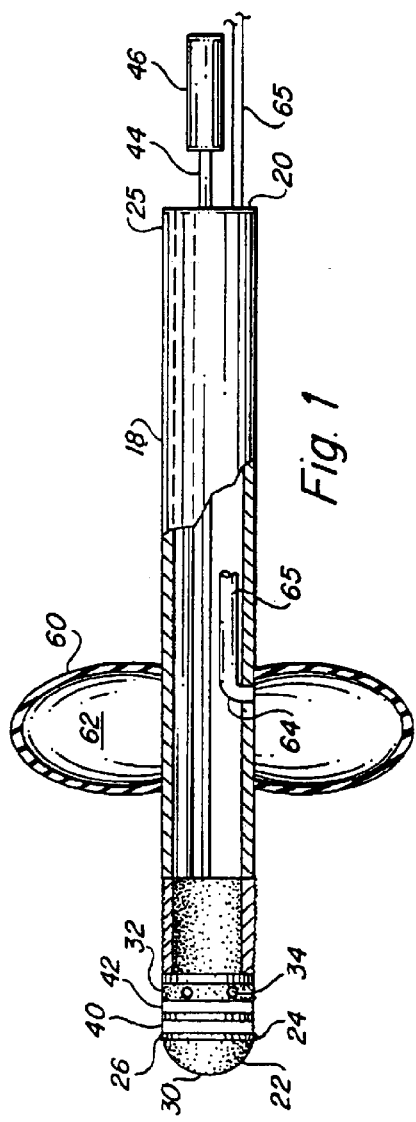
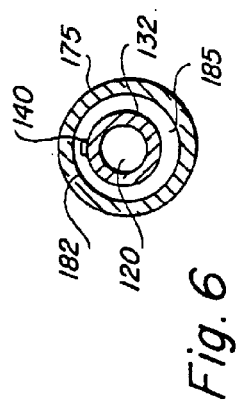
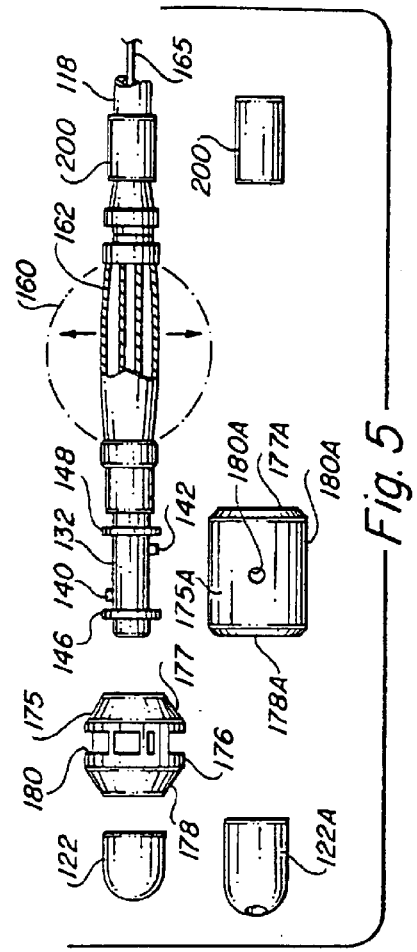
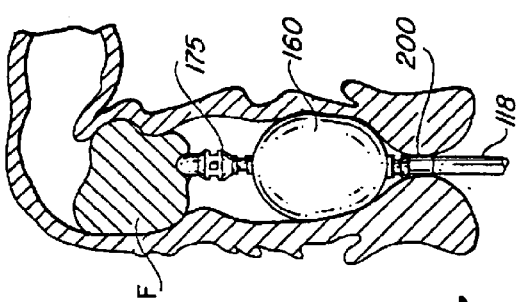

BOWEL PROBE & METHOD FOR CONTROLLING BOWEL INCONTINENCE

CROSS REFERENCE TO PRIOR APPLICATION

This application is based on provisional application Ser. No. 60/313,540 filed Aug. 20, 2001, of the same title.

FIELD OF THE INVENTION

The present invention relates to a system for controlling episodes of bowel incontinence and more particularly relates to a probe for detecting the presence of fecal mass in the rectum.

BACKGROUND OF THE INVENTION

Fecal incontinence is a disabling and distressing condition. Many patients have little or no control over bowel movements. This condition can be embarrassing resulting in curtailed activities and limited social involvement. In addition, bowel incontinence presents problems to nursing homes and caretakers as attending personnel are required to remove and replace soiled linens, blankets and gowns and are often required to bathe the patient after an episode. These tasks are unpleasant and also require substantial time and effort on the part of attending personnel. Increased monitoring of patients is also necessary to prevent infections due to prolonged contact with fecal material on the skin surfaces.

There are several approaches to the problem of bowel incontinence. A simple and commonly used technique is the use of absorbent, disposable pads to protect the bed and the patient. Use of pads may minimize the time required on the part of attending personnel after an episode but pads do not in any way serve to detect or prevent such episodes.

Many patients suffering from this condition may show a significant improvement of their symptoms either with conservative medical treatment or surgery. Various types of surgeries are performed to remedy this condition including sphincter repair, gracilopalsty, and gluteoplasty.

However, there are a considerable number of patients who have had surgical treatments that have failed. In some instances surgery is inappropriate due to the patient's poor general medical condition or as a result of a personal choice on the part of the patient.

One non-surgical approach to the problem of fecal incontinence is bio-feedback. The success rate for bio-feedback approaches to bowel incontinence is variable and may not be of significant long-term value to a patient with isolated deficiency in internal sphincter function.

Another non-surgical approach has been to provide devices that sense the presence of fecal material in the human colon. Such devices are designed to provide the patient and attendants sufficient time and warning so that the patient will be able to act to avoid an embarrassing or unpleasant episode.

Japanese Patent Publication 101569182 discloses a method and device for detecting fecal material. The purpose is to prevent incontinence of a patient confined to a bed by detecting the presence of fecal matter in the colon from the intensity difference of reflected light from the fecal material. The remote end section of a disposable probe is attached to a coupling member and is inserted into the colon by using a hypodermic syringe. When a sensor at the forward end of the probe comes into contact with fecal material, a tip formed as a flexible end cap and a flexible reflection strip composed of Mylar are deformed. Light is directed to the strip from a control unit through a fiberoptic cable and the intensity of the instant light and the reflected light are sampled and compared. When the signal variation is larger than the prescribed value, an audible or visual warning signal is provided to alert the patient and attendants.

Another bowel probe and method for controlling bowel incontinence is shown in U.S. Pat. No. 4,813,422. This patent discloses a bowel control apparatus and method for sensing and preventing incontinent episodes. The probe comprises a catheter with an infrared (IR) sensor tip for sensing fecal mass in the rectum and a cuff which is inflated to prevent passage of the fecal mass. The method of sensing and preventing incontinent episodes include the steps of inserting the probe in the rectum, inflating the cuff, transmitting IR light into the rectum, monitoring the reflectance of IR light and generating an alarm signal when a predetermined amount of IR light is measured.

While devices, as described above have, to some extent, been successful in detecting a potential incontinent condition and generating an alarm, the use of optical or light reflecting systems in such an environment are not always reliable. Further, it has been found that use of inflatable cuffs without sensors to block discharge of fecal mass until the patient reaches a bathroom may have the potential, over prolonged time, to cause damage to the rectal tissue and restrict capillary blood flow.

It is therefore an object of the present invention to provide an improved apparatus and method for sensing the presence of fecal matter in the human colon.

It is another object of the present invention to provide an apparatus and method for detection of a potentially incontinent condition to a patient and to generate an alarm, either a local alarm or centralized alarm, to alert nursing or attending medical personnel to the condition.

It is a further object of the present invention to provide a method and apparatus for detecting an incontinent condition and when detected will temporarily block the discharge of fecal matter in a manner to minimize injury or irritation to the rectal tissue even over prolonged periods of usage.

BRIEF SUMMARY OF THE INVENTION

Briefly, the present invention provides a catheter-like probe fabricated from a biochemically inert material which defines a lumen. The distal tip of the probe is configured for ease of insertion into the rectum and incorporates a pair of spaced-apart conductivity sensors which are connected to a monitoring system through electrical wires extending through the lumen or along the probe. The presence of fecal matter will complete a circuit between the conductivity sensors causing an electrical signal to be to monitoring equipment. The conductivity sensors may be spaced-apart, conductive rings or point contacts enclosed within an aperture sleeve which sleeve may be removed for cleaning. The signal will activate an alarm to alert attending medical personnel to an impending incontinent episode. The alarm device may be a pager device located at the patient which may also be capable of sending a remote signal to a centralized monitoring station.

The distal tip of the probe further incorporates flatus venting means which may be ports or vent holes in the distal end or, in the alternative, a portion of the probe may be a porous material which will allow gas to vent through the lumen. Lumen may incorporate a filter of charcoal or other odor eliminating material. An expandable, annular sealing sleeve extends abut the probe and is located so that when inserted, the sealing sleeve is positioned in the area of the anus.

Located at an intermediate location between the distal and proximate ends of the probe is an inflatable cuff similar to that found on bladder-type catheters. The cuff is inflatable to block the rectum entrance preventing discharge of fecal matter from the colon until the patient reaches a bathroom. The bladder cuff may be connected to an air-pulsing system having an air pressure reservoir or plenum chamber connected to an air pump across a check valve. A valve is connected to the air supply reservoir. The cuff is inflated by air from the air supply reservoir to a predetermined volume as for example 20 cc of air. The valve will allow the cuff to slowly deflate over a period of time, as for example to 18 cc volume in one hour. The pump then activated to re-inflate the cuff to a predetermined volume. The pulsating or cyclic deflation and inflation of the cuff will stimulate rectal tissue preventing necrosis of rectal tissue and prevent unnecessary or undue restriction of capillary blood flow in the rectum.

When a patient is able to care for himself or herself, the patient can be provided a pager-type device which will alert the patient and nearby care-givers of an impending episode by providing an alarm. When the patient is dependent upon a care-giver or nurse, the alert signal from the probe can be transmitted by an RF signal or a hard wire such as a telephone line to a centralized PC station providing an alert to attending personnel to provide an attendant. The PC can monitor and track a large number of patients using probes according to the invention. If the patient is receiving home care, the probe signal may be transmitted to a pager carried by a home care attendant.

BRIEF DESCRIPTION OF THE DRAWINGS

The above and other objects and advantages of the present invention will be more apparent from the following description, claims and drawings in which:

FIG. 1 is a perspective view partly broken away showing an embodiment of the rectal probe of the present invention;

FIG. 5 is an exploded detail view of the distal end of the probe of FIG. 4;

FIG. 6 is a cross-sectional view taken along line 6—6 of FIG. 4; and

FIG. 7 is a view of the colon and rectum of a patient with the probe inserted and in an inflated condition.

DETAILED DESCRIPTION OF THE INVENTION

Figure 3:
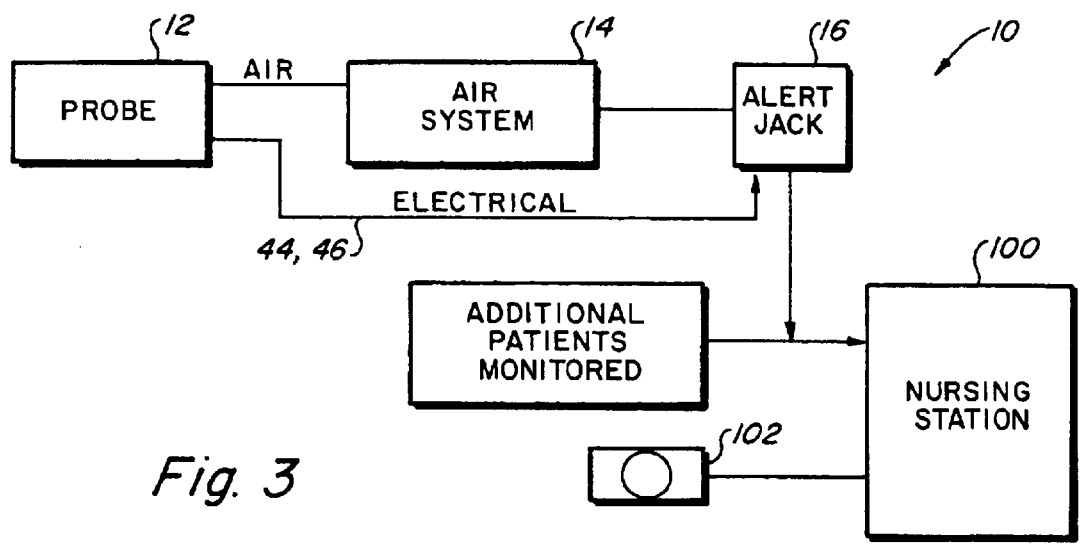
FIG. 3 is a schematic of the monitoring system which may be connected to the probe.

Turning now to the drawings, particularly FIG. 3, the system of the present invention is schematically diagrammed and is generally designated by the numeral 10 and includes a probe 12, an air system 14 and an alert system 16. The probe is intended for insertion by medical personnel or, even in some cases, may be self-inserted by the patient after the procedure is demonstrated and practiced. The probe is normally inserted so the tip is at the rectosigmoid junction in the human colon as seen in FIG. 6. Generally the device is inserted approximately 8 centimeters into the rectum. After insertion, a balloon cuff on the probe is inflated with approximately 20 cc of air using a common plastic syringe or squeeze bulb. The probe is then withdrawn until it encounters resistance afforded by the anal sphincter. This procedure allows either the patient or medical personnel to determine if the balloon is sufficiently inflated and is correctly positioned with the tip free in the rectal ampulla proximate to the anal canal. An expandable sealing sleeve extends about the probe in the area of the anus. Once in place, the probe is connected to the air and alert systems. The alert system may be connected to a nursing station 100 and a computer 102. Multiple patients may be monitored in this manner. The system and its components will be described in greater detail below.

Turning now to FIG. 1, the probe 12 has an elongate, flexible, catheter-like, tubular body 18 which defines an internal lumen 20. The material of the body of the probe is any suitable bio compatible material such as a medical grade C-flex or silicon rubber. Materials such as C-flex are non-reactive and provide a comfortable surface permitting relatively easy insertion and removal of the device. The probe is elongate and slightly flexible and sized for insertion in the human rectum through the anus. The diameter typically is about 0.25 to 0.37 inches.

The end of the probe body is enclosed by a cap or tip 22. The cap or tip is also formed from a suitable medical grade bio-compatible material such as those sold under the trade name C-flex or Pellethane. The tip has an annular lower edge 24 and defines a recess 26 which receives the end of the body of the probe. The tip 24 may be secured to the body by suitable techniques such as sonic welding or application of a suitable adhesive, but preferably is engaged by a snug friction fit so it may be removed. The end 30 of the tip 22 is generally a tapered cone or rounded for ease of insertion. Preferably the tip 22 has a shape similar to that used in suppositories.

A section 32 of the probe adjacent the tip may be provided with vent holes 34, but preferably section 32 of the probe body is fabricated from a suitable porous material such as that sold under the name Porex. Porex and similar materials, such as ePTFE, are preferred because they are pervious to gases and impervious to liquids. The expanded Porex material will allow passage of gas into the lumen 20 of the probe so the gas will vent at the proximal end 25 of the probe. The porosity eliminates the need for separate vent holes in the body of the probe.

A filter 28 of charcoal or similar odor absorbing material is disposed within the lumen at a location inward of the tip. The filter may be disposable to allow re-use of the probe without porous materials becoming clogged or being a source for bacterial growth.

The probe is designed so as to be re-usable so long as the porous tip 22 is removed and replaced to avoid bacterial contamination and the probe is thoroughly cleaned between uses. The re-usable feature is important to provide a low-cost solution to the chronic problem of bowel incontinence.

Disposed inward of the tip are a pair of spaced-apart sensors 40, 42. The sensors are shown as annular rings extending annularly around the body of the probe and are made of a suitable conductive material such as copper, stainless steel, platinum, iridium or other bio-compatible material. The annular rings may be formed by winding several or more wraps of wire around the body of the probe. The sensors 40, 42 are connected to electrical conductors 44, 46 which extend through the lumen exiting the proximal end 25. The conductors 44, 46 at the proximal end are connected to a monitoring and air system unit as will be described hereafter. Typically, the sensors are spaced about 6.0 to 15.0 millimeters apart, although the spacing may vary. A low voltage current is transmitted from the alert system 16 to one of the conductivity sensors, as for example, along wire 44.

When fecal mass is not present within the proximity of the conductivity sensors, the circuit is open and no current is passed through the return wire 46 to the alert system 16. When fecal mass is present within the proximity of the conductivity sensors, an electrical conductivity path will be established between the sensors 40, 42 and the circuit is completed sending a signal through wires 44, 46. The low voltage electrical signal transmitted is utilized to activate an alarm warning of an impending episode of bowel incontinence. Preferably the signal is directed to a microprocessor 52 such as a ATMEL processor (Model No. AT90LS8535-4 AC) which will control the alarm function.

Referring again to FIG. 1, an inflatable annular cuff or bladder 60 extends about the probe body at an intermediate location approximately 1.0 to 3.0 centimeters from the distal end of the probe. The cuff is attached by an adhesive or other bonding or welding techniques such as ultra sonic welding or by molding the cuff and probe body as an integral part. The cuff or balloon defines an air chamber 62 made from a suitable elastic material such as a medical grade silicon rubber, latex, polyethylene or C-flex. The cuff accomplishes several important functions. First, the cuff will serve to hold the probe in position in the bowel preventing it from being inadvertently withdrawn. The cuff 60 will also provide a physical obstacle or barrier to prevent the uncontrolled passage of fecal mass as the cuff serves as a physical block within the colon adjacent the anus.

The cuff 60 has an opening 64 which serves both as an air inlet and outlet which is connectable to an air module by means of an air tube 65 within the lumen of the catheter probe body. The cuff 60 cooperates with the air system 14 to regulate air pressure within the cuff. Typically, cuff 60, in an inflated condition, will have a volumetric capacity of approximately 20 cc. As will be explained hereafter, the air system will periodically inflate the cuff to the fully inflated volumetric capacity and then allow the cuff to slowly deflate over a period of time. The cyclic or pulsating inflation and deflation will stimulate the rectal tissue avoiding necrosis of the rectal tissue and will allow capillary blood flow in the rectal area.

Figure 4:
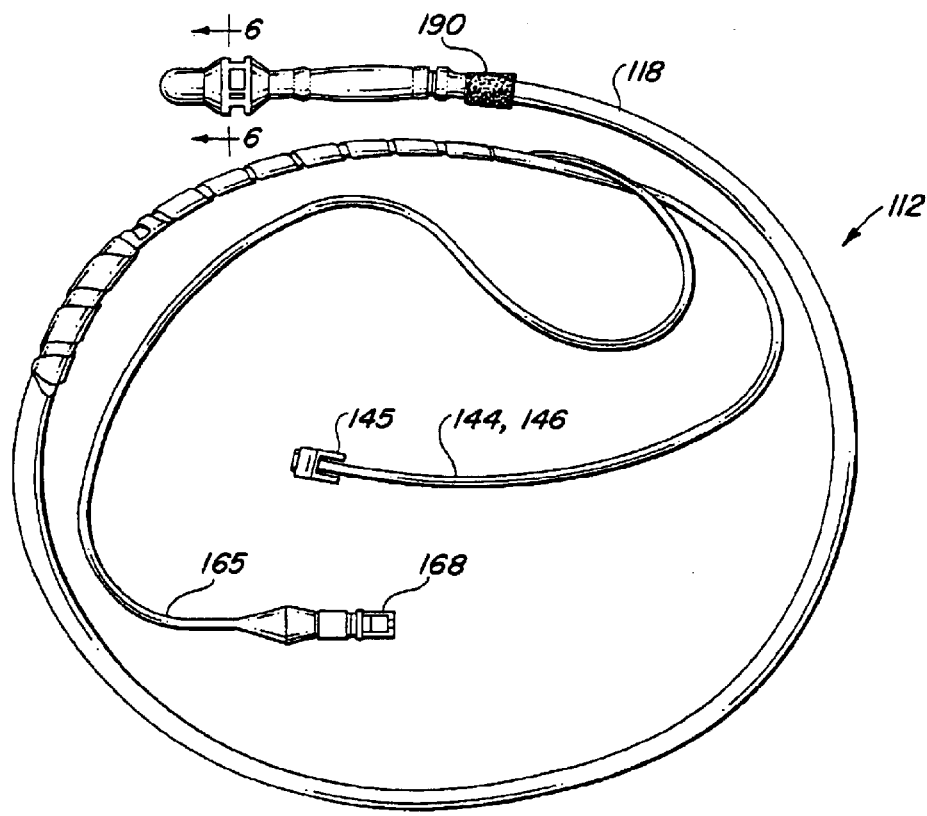
FIG. 4 is a perspective view showing another embodiment of the probe.

Referring to FIGS. 4, 5 and 6, an alternate embodiment of the probe is shown designated by the numeral 112 having an elongate, flexible tubular body 118 defining a lumen 120. The body is a suitable medical grade material such as C-Flex or silicone rubber and is sized for rectal insertion.

The distal end of the tube has a section 132 in which are located a pair of axially spaced-apart and diametrically opposed point sensors 140, 142. Section 132 is a rigid medical grade plastic. The sensors are electrically conductive and are connected to conductor wires 144, 146 which connect to a monitoring unit at a connector 145 such as alert system 16 as described above at jack 94. The end of section 132 is open and annular flange 146 extends around the opening to receive removable filter tip 122. Tip 122 is a porous material such as Porex and has a rounded or tapered exterior and snugly engages the end of section 132 abutting flange 146. Flange 148 extends around the proximal end of section 132.

An annular cuff or bladder 160 extends about the probe body adjacent section 132 approximately 1.0 to 3.0 cm from the distal end. The cuff 132 is an elastic material such as medical grade silicone rubber, latex, polyethylene or C-Flex. The cuff has an opening 162 which is connected to air system 14 by an air tube 165 extending in the lumen 120. The bladder may be initially inflated using a syringe and then connected to the air system at connector 168 and thereafter cyclically deflated and inflated during use as described to stimulate tissue in the rectal area.

A protective sleeve 175 extends about section 132 and the electrical sensors. Sleeve 175 is shown in detail in FIGS. 5 and 6 and has a cylindrical body 176 with tapered ends 177, 178. The body defines slots 180 which intercept central bore 182. The bore 182 is slightly greater in diameter than the diameter of section 132 defining an annular clearance space 185. In position, the sleeve abuts flange 148. The purpose of the sleeve is to shield the sensors 140, 142 to prevent false alarms from moisture in the rectum. The sleeve 175 partially shields the sensors so that when an episode occurs, fecal matter "F" as seen in FIG. 7 will enter the slots 180 and migrate to the annular area 185 between the sleeve and the sensors which will result in an electrical circuit being completed and an alarm emitted. The sensors are shielded sufficiently so that false alarms from incidental moisture are avoided.

In FIG. 5, an alternate sleeve 175A having a body 180A with tapered ends is shown having a circular bore 180A, rather than slots, extending to the interior bore. Tip 122A is similar to tip 122 but slightly elongated.

The tubular body 118 is provided with a seal 190 positioned to align with the anus in the inserted position. The seal 190 is a expandable medical grade material such as medical grade cosmetic foam shown as an annular sleeve adjacent the cuff. The seal may be slidable along the body so its position may be adjusted. The seal, as seen in FIG. 7, seats in the anus to provide additional leakage protection.

The design of the alternate embodiment permits convenient re-use. Upon removal, the tip 122 is removed and discarded. The sleeve 175 is cleaned and sanitized. The probe is cleaned and sanitized. A new tip and cleaned sleeve are attached and the clean probe is ready for re-use with the same patient resulting in substantial cost saving.

Figure 2:
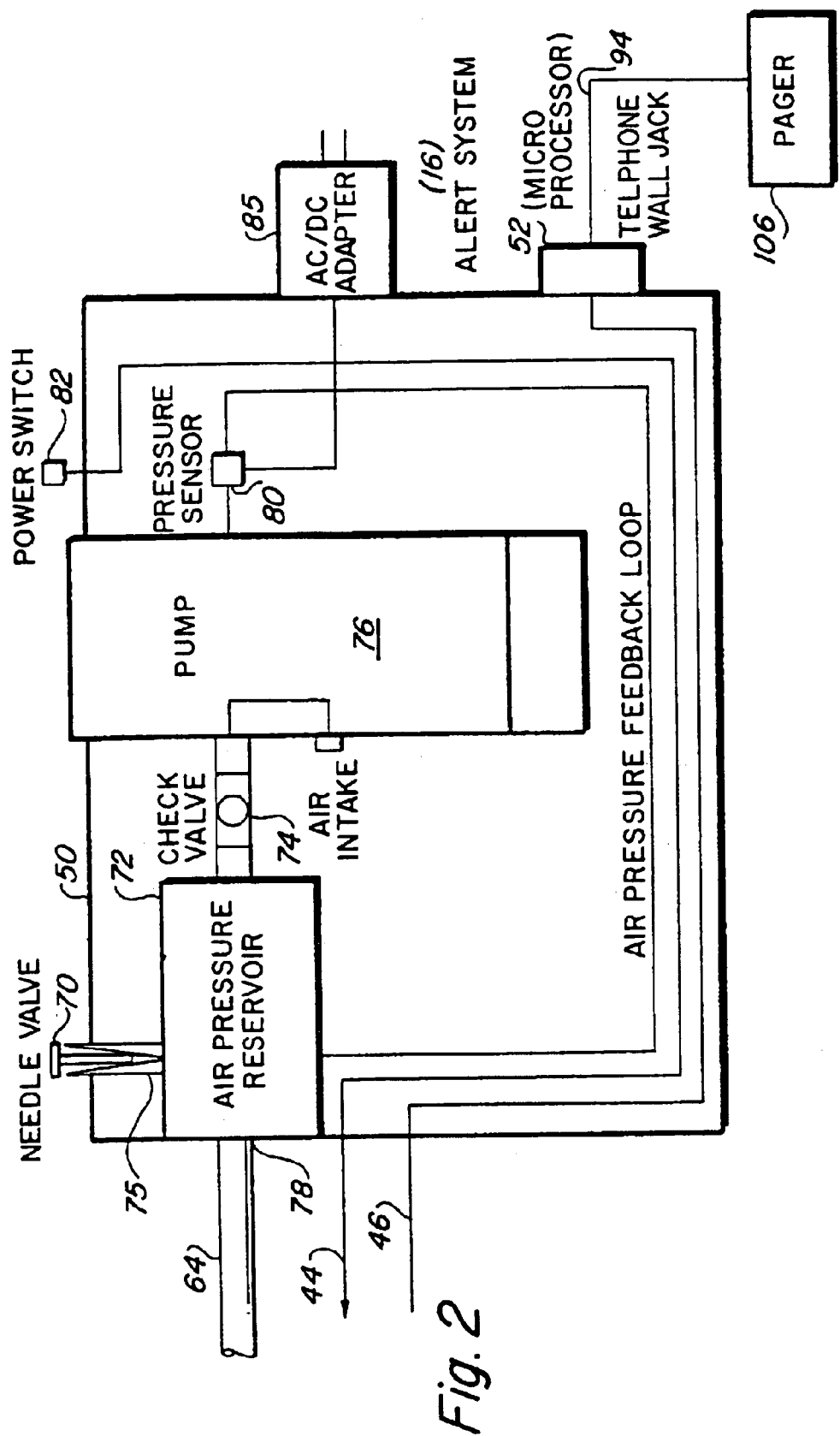
FIG. 2 is a schematic view of the air pulsating system.

Turning now to FIG. 2, the schematic diagram of control module 14 is shown use of the system will be described with reference to the probe as shown in FIGS. 4, 5 and 6. As seen, the air system 14 has an air pressure chamber 72 connected to a small air pump 76 across a check valve 74. The air pump 76 may be of the type manufactured by Micro Air Pumps. The air pressure chamber has an outlet 78 which is connectable at a suitable fitting to the probe air tube at connector 168. A small needle valve 70 is received within an air bleed port 75 in chamber 72. The needle valve can be manually set to allow a predetermined volume of air to bleed over a period of time. The air pump 76 is connected to a source of power such as an AC/DC wall adaptor 85, or a rechargeable battery. The power is controlled by the pressure sensor 80.

The pressure sensor 80 is set at a predetermined level or set point. Once the power 82 switch is turned on, the pressure sensor will control the pump so as to deliver air to the air chamber until a suitable level of inflation has occurred in the inflatable cuff. Once this has occurred, the pressure sensor will shut the pump off. Alternatively, the cuff may be manually inflated and then connected to the air system. The pressure sensor is set, for example, at a maximum setting of 20 cc volumetric and set to activate the pump, for example, when the air volume falls below 18 cc in the cuff. Thus, when the cuff is inflated to full volumetric capacity, the pump will be caused to shut off. This will allow the bleed needle valve 78 to slowly release air from the air chamber and, accordingly, from the cuff to which is in communication with the air chamber.

Over a prescribed period of time, as for example one hour, the cuff 160 will be allowed to deflate to a minimum volumetric capacity. Once this capacity is reached, the pressure sensor 80 will again activate the pump sensing the diminished pressure via feedback loop 88. Therefore, over a period of time the cuff will cyclically inflate and deflate which will gently massage the area contacted by the cuff to stimulate blood flow and the tissue in the rectum.

The alert system 14 receives the alert signal from the probe once a current is detected and a circuit completed in wires 144, 146. Upon alert signal being received at the microprocessor 52, a suitable signal will be emitted by the module so either the patient or attending medical personnel can promptly attend to the patient. If the patient is bedridden, the alert signal can be connected to a hard wire connection such as a telephone wall jack 94 which will, in turn, be received at a remote nursing station 100 a seen in FIG. 3. Alternatively, the module may contain a radio frequency (RF) transmitter 104 which will transmit a wireless signal to the nursing station 100.

The probe system of the present invention can also be used as a portable unit for ambulatory patients. In this application, the system 16, is contained in a compact module, which can be transported with the patient, in a wheel chair or on a suitable carrier stand. The source of power would be a DC source of power such as a battery connected to adapter 85. The patient may be equipped with a device such as a pager 106 which is connectable to the alert signal at jack 94, which pager device will provide an audible or vibratory signal to the patient of an impending episode and which also could be transmitted to a central station.

In FIG. 3, a central nursing station 100 is shown connected to receive alert signals from a plurality of patients within a network. Each alert signal is a discreet signal which will identify the particular patient or location from which the signal emits. Further, a cental computer 102 can store suitable patient information and profile and including identification of the patient, responding attendant, response time and type of episode in the time of episode. Such information will greatly assist personnel in properly treating the patient and also reduce the potential liability of medical care facilities and personnel.

The system also has a fecal accident prevention feature. If the conductivity sensors should detect the presence of fecal matter in the lower cavity in the rectum chamber while the balloon is in the deflation mode, the air pump will be activated immediately bringing the balloon to full inflation to maintain full inflations to block passage of fecal matter.

Thus, it will be seen that the present invention provides a probe which will be effective in preventing fecal episodes and will also improve the quality of patient lives. The probe should also reduce the cost of attending medical care, reduce potential liability issues, and provide increased response time and provide more accurate medical records.

It will be obvious to those skilled in the art to make various changes, alterations and modifications to the invention described herein. To the extent such changes, alterations and modifications do not depart from the spirit and scope of the appended claims, they are intended to be encompassed therein.

I claim:

1. A device for insertion into the human rectum to monitor bowel incontinence by detecting the presence of fecal material comprising:
    (a) a probe body defining a lumen having a distal and proximal end wherein at least a portion of said probe body defines venting means to allow venting of flatus;
    (b) said distal end having a tip;
    (c) conductivity sensor means on the exterior of said probe body near said distal end, said sensor means being connectable to an electrical circuit to establish an alert signal in the presence of fecal material; and
    (d) an inflatable cuff extending about said probe body at a location on said probe body spaced from said sensor means.

2. The device of claim 1 wherein said sensor means comprise spaced-apart conductors.

3. The device of claim 1 wherein said cuff is connected to a source of pressurized air.

4. The device of claim 3 wherein said source of pressurized air includes a pump and pressure sensor means which will cyclically operate said pump to inflate and deflate the cuff between predetermined volumetric levels.

5. The device of claim 1 wherein said venting means comprises a gas permeable material.

6. The device of claim 5 wherein said gas permeable material is ePTFE.

7. The device of claim 1 further including a monitoring station communicating with said electrical circuit.

8. The device of claim 7 wherein said monitoring station includes a computer.

9. The device of claim 8, wherein said monitoring station is networked with a plurality of devices for insertion into the rectum of patients.

10. The device of claim 1 further comprising means for transmitting said alert signal to a care-giver at a remote location.

11. The device of claim 1 wherein said tip is configured for ease of insertion into the rectum.

12. The device of claim 1 wherein said sensor means are axially spaced-apart conductive means.

13. The device of claim 1 wherein said conductive means are conductive rings.

14. The device of claim 13 wherein said sensors are shielded by a perforated sleeve.

15. The device of claim 12 wherein said sensor are conductive point contacts.

16. A method for detecting and controlling bowel incontinence comprising:
    (a) providing a rectal probe having a distal and proximal end and defining a lumen;
    (b) providing conductivity sensors on said probe which are connectable to a alert unit, said sensors positioned so an electrical circuit is completed in the presence of fecal matter which will activate an alarm;
    (c) providing an inflatable cuff on said probe;
    (d) inserting the probe and cuff in the patient's colon; and
    (e) cyclically inflating and deflating the cuff to retain the probe in position and to block passage of fecal matter and to stimulate the rectal area.

17. The method of claim 16 wherein said circuit is connected to a remote monitoring system.

18. The method of claim 17 wherein a plurality of patients are connected to said remote monitoring system.

19. A device for insertion into the human colon to monitor bowel incontinence by detecting the presence of fecal matter comprising:
    (a) a generally flexible tubular probe body defining a lumen, said body having a proximal and distal end;
    (b) conductivity sensor means on the exterior of said probe body adjacent said distal end, said sensor means being connectable to an electrical circuit which will transmit an alert signal in the presence of fecal matter;

(c) a removable sleeve extending about said sensor means, said sleeve partially shielding said sensor means to prevent false alarms; and (d) an inflatable cuff extending about said probe body connectable to an air supply.

20. The device of claim 19 further including means for periodically inflating and deflating said cuff.

21. The device of claim 19 including sealing means on said probe body positioned to generally seat in the anus when the probe is inserted into the human colon.

22. The device of claim 19 wherein said sleeve has a generally cylindrical body with a bore selected to define an annular space between said cylindrical body and said sensor and wherein said cylindrical body defines an aperture to allow fecal matter to pass into said annular space.

23. The device of claim 19 further including a replaceable tip on the distal end of said probe body.

* * * * *